United States Patent [19]

Ambler

[11] 4,321,119

[45] Mar. 23, 1982

[54] BUFFER COMPOSITION AND METHOD FOR THE ELECTROPHORETIC SEPARATION OF PROTEINS

[75] Inventor: Jeffrey Ambler, Tollerton, England

[73] Assignee: Gelman Sciences, Inc., Ann Arbor, Mich.

[21] Appl. No.: 92,249

[22] Filed: Nov. 7, 1979

[51] Int. Cl.$^3$ .................... B01D 57/02; G01N 33/68; A61K 31/60

[52] U.S. Cl. ........................... 204/180 R; 204/180 S; 252/408; 252/500; 424/230

[58] Field of Search ........................ 204/180 S, 180 R; 424/230; 252/500, 408

[56] References Cited

U.S. PATENT DOCUMENTS 3,686,087 8/1972 Vestermark ..................... 204/180 S
4,146,454 3/1979 Haber ............................. 204/180 S

OTHER PUBLICATIONS

Bates et al., J. Res. Nat'l. Bur. Stand. vol. 32 pp. 131, 132 (1944).
The Book of pH, by Webber, p. 94, pub. by George Newnes Ltd., London (1957).
Electrophoresis and Immunoelectrophoresis by Cawley, pp. 330–332, pub. by Little, Brown & Co. Boston (1969).

*Primary Examiner*—F. Edmundson
*Attorney, Agent, or Firm*—Reising, Ethington, Barnard, Perry & Brooks

[57] ABSTRACT

A non-barbiturate buffer composition for use in the electrophoretic separation of proteins into fractions, the buffer composition consisting essentially of a water soluble salicylate, a water soluble inorganic salt such as sodium chloride, and buffer to maintain the pH at from about 8.2 to 9.0.

7 Claims, No Drawings

BUFFER COMPOSITION AND METHOD FOR THE ELECTROPHORETIC SEPARATION OF PROTEINS

TECHNICAL FIELD

The subject matter of the present invention is a buffer composition and method for the electrophoretic separation of proteins into fractions. The buffer composition and method of the present invention find particular utility as replacements for electrophoretic procedures and buffers which are currently used for the separation of proteins and which involve the use of barbiturates.

BACKGROUND ART

It is well known that a protein material can be separated into different fractions of different densities, by electrophoresis. In the practice of this technique the protein sample to be fractionated is placed on the surface of a substrate which is immersed in, or otherwise saturated with, a so-called buffer solution, whereupon an electrical current is applied sufficient to cause migration, by way of electrophoresis, of the protein material into fractions of different mobilities, the fractions being spaced from each other, on the substrate, between the anode and the cathode. After the separation is complete, it then only becomes a matter of determining the relative quantities of the fractions by any of various techniques equally well known in the art.

The buffer solution currently in common use for such protein analysis includes a barbiturate as its key ingredient. That is, the buffering function is provided by a combination of barbituric acid and a salt of barbituric acid. The main disadvantage to this has been, and continues to be, that the barbiturates are "controlled substances" under the drug control laws and regulations of the United States, and under similar laws and regulations of other countries. Hence, in the manufacture, distribution, sale and use of such buffers, accountability and administrative control are required, with much attendant trouble and expense. It is particularly for this reason that there has been a long felt need for a non-barbiturate buffer composition which is as effective as the currently used barbiturate buffers for the electrophoretic separation of protein materials.

The present invention fulfills this need.

DISCLOSURE OF INVENTION

Briefly, what I have discovered is that if a water soluble salicylate such as sodium salicylate is used in combination with a water soluble inorganic salt, such as sodium chloride, and a buffer to maintain the pH at from about 8.2 to 9.0, there results a buffer solution which, though it doesn't involve the use of barbiturate or any other controlled substance, is as effective as, and in some respects superior to, the barbiturate buffers heretofore used in the electrophoretic separation of proteins.

The preferred buffer is a combination of Tris [2-amino-2-(hydroxymethyl)-1,3-propanediol] and Tricine [N-tris(hydroxymethyl)methylglycine], though other buffers can be used within the purview of the invention.

I theorize, and the test results appear to verify that the salicylate functions as a complexing agent in the buffer solution, forming a bond—probably by way of hydrogen bonding—to the protein thereby affecting the mobility of the protein in migration during the electrophoresis. The alkali metal salts of salicylic acid are preferred because of their relative high solubility in water; however it is within the purview of the invention to use other water soluble salicylates. The salicylate need be present only in relatively small amount, preferably from about 0.5 to 1 gram per liter of solution, which is ample to complex with all the protein present during the electrophoresis.

The function of the inorganic salt is to provide the solution a high ionic concentration and hence increased current carrying capacity. The preferred salts are the alkali metal halides, though other ionized inorganic salts can be used. It is preferred that the salt be present in an amount from about 1.5 to 3 grams per liter of solution and most preferably about three times the amount of the salicylate.

It will be understood, of course, that the amount of buffer used must be sufficient to maintain the pH of the solution at from 8.2 to 9.0 throughout the electrophoretic procedure in which the solution is used. Where Tris-Tricine is used as the buffer, it is preferred that the Tricine be present in an amount of from about 2 to 5 grams per liter and that the Tris be present in an amount approximately one and one half to two and one half times the amount of the Tricine.

For the practice of the invention it is generally preferred, as a matter of convenience, to prepare a mixture of the salicylate, inorganic salt and buffer in solid, dry form with the ratio of the salicylate, the inorganic salt and buffer being such that when sufficient of the mixture is dissolved in water to provide the preferred salicylate concentration of from 0.5 to 1 gram per liter, the amount of the inorganic salt present in the solution will be from about 1.5 to 3 grams per liter and the amount of buffer in the solution will be such as to provide a pH from 8.2 to 9.0.

As has been indicated above, the buffer compositions of the present invention are intended to replace the currently used barbiturate buffering compositions, and they can be used in all electrophoretic procedures and with all substrates where barbiturate buffering solutions are or have been used. Hence, the substrate used can, for example, be agarose gel or membrane such as cellulose acetate membrane; and the electrophoretic procedure can be either one of zone electrophoresis or one of immunoelectrophoresis. For example, using agarose, the buffer may be used for electrophoresis systems which identify lipoproteins, proteins or isoenzymes. The buffer may also be used to support systems in which immunoelectrophoresis techniques are carried out, either by fixation, diffusion, or electrodiffusion. Such techniques, for example, as the Rocket technique of Laurel, may be carried out with equal success on agarose or cellulose acetate membrane.

BEST MODE FOR CARRYING OUT THE INVENTION

The most preferred composition of the present invention contains the following as its essential ingredients, in amounts to provide, when dissolved in water, the amount per liter indicated for each ingredient:

| | |
|---|---|
| Tris | 8.0 g/l |
| Tricine | 3.75 g/l |
| Sodium Chloride | 2.25 g/l |
| Sodium | |

| -continued | |
|---|---|
| Salicylate | 0.75 g/l |

The following is a typical electrophoretic method wherein the immediately aforesaid composition is used for the buffer solution:

A cellulose acetate membrane is equilibrated with the buffer solution for at least 10 minutes prior to use whereby it is saturated with the solution. After removing excess moisture from the surface, the membrane is placed in a conventional electrophoresis chamber, making contact at either end with the buffer solution present in the two electrode compartments of the chamber. The sample is applied and electrophoresis carried out at a suitable voltage (typically 175–225 volts) and for a suitable time (typically 20–30 minutes) thereby to cause the separation of the protein sample into fractions. The sample separation is then stained with a protein stain such as Ponceau S, the membrane is cleared and the protein fractions quantitated using a densitometer. Five protein fractions are obtained in the same manner as with barbiturate buffer, so that reliable quantitation may be carried out. In addition to the fact that the buffer is composed of non-dangerous components it has advantages over barbiturate in other regards, particularly in that it dissolves more quickly, is more stable at room temperature and it prevents or at least more strongly inhibits the electroendosmosis effect.

It will be understood that while the invention has been described in its particulars with reference to preferred embodiments, various changes and modifications may be made all within the full and intended scope of the claims which follow:

What is claimed is:

1. A composition for the preparation of a buffer solution for use in the electrophoretic separation of proteins, said composition consisting essentially of a water soluble salicylate, a water soluble alkali metal salt to increase the ionic concentration of the solution, and buffer sufficient to maintain the pH of the solution at from 8.2 to 9.0 during the electrophoresis.

2. A composition as set forth in claim 1 wherein the specified ingredients are present in a ratio of about 0.5 to 1 grams salicylate to about 1.5 to 3 grams inorganic salt.

3. A composition as set forth in claim 1 wherein the water soluble salicylate is sodium salicylate, the water soluble alkali metal salt is sodium chloride, and the buffer is a combination of 2-amino-2-(hydroxymethyl)-1,3-propanediol and N-tris(hydroxymethyl)methylglycine.

4. A composition as set forth in claim 3 containing the specified ingredients in a ratio of about 8 grams 2-amino-2-(hydroxymethyl)-1,3-propanediol to about 3.75 grams N-tris(hydroxymethyl)methylglycine to about 2.25 grams sodium chloride to about 0.75 grams sodium salicylate.

5. An aqueous electrically conductive solution for use as a buffer solution in the electrophoretic separation of proteins, said aqueous solution containing from about 0.5 to 1 grams per liter water soluble salicylate, from about 1.5 to 3 grams per liter water soluble alkali metal salt to increase the ionic concentration of the solution, and buffer sufficient to maintain the pH of the solution at from 8.2 to 9.

6. An aqueous solution as set forth in claim 5 containing, as buffer, 2-amino-2-(hydroxymethyl)-1,3-propanediol and N-tris(hydroxymethyl)methylglycine.

7. An aqueous solution as set forth in claim 6 wherein the water soluble salicylate is sodium salicylate and is present in an amount of about 0.75 grams per liter, wherein the water soluble alkali metal salt is sodium chloride and is present in an amount of about 2.25 grams per liter, wherein the 2-amino-2-(hydroxymethyl)-1,3-propanediol is present in an amount of about 8 grams per liter and wherein the N-tris(hydroxymethyl)methylglycine is present in an amount of about 3.75 grams per liter.

* * * * *